(12) United States Patent
Choudhary et al.

(10) Patent No.: US 11,939,352 B2
(45) Date of Patent: Mar. 26, 2024

(54) POTENT AROMATASE INHIBITORS THROUGH FUNGAL TRANSFORMATION OF ANTI-CANCER DRUG TESTOLACTONE: AN APPROACH TOWARDS TREATMENT OF BREAST CANCER

(71) Applicants: Muhammad Iqbal Choudhary, Karachi (PK); Atia-tul Wahab, Karachi (PK); Mahwish Siddiqui, Karachi (PK); Nimra Naveed Shaikh, Karachi (PK); Sammer Yousuf, Karachi (PK); Atta-ur Rahman, Karachi (PK)

(72) Inventors: Muhammad Iqbal Choudhary, Karachi (PK); Atia-tul Wahab, Karachi (PK); Mahwish Siddiqui, Karachi (PK); Nimra Naveed Shaikh, Karachi (PK); Sammer Yousuf, Karachi (PK); Atta-ur Rahman, Karachi (PK)

( * ) Notice: Subject to any disclaimer, the term of this patent is extended or adjusted under 35 U.S.C. 154(b) by 0 days.

(21) Appl. No.: 17/177,209

(22) Filed: Feb. 17, 2021

(65) Prior Publication Data

US 2021/0230214 A1    Jul. 29, 2021

(51) Int. Cl.
| | | |
|---|---|---|
| *C07D 311/78* | (2006.01) | |
| *A61K 31/366* | (2006.01) | |
| *A61K 31/585* | (2006.01) | |
| *A61P 35/00* | (2006.01) | |
| *C07D 493/04* | (2006.01) | |
| *C07J 73/00* | (2006.01) | |

(52) U.S. Cl.
CPC ............. *C07J 73/003* (2013.01); *A61P 35/00* (2018.01)

(58) Field of Classification Search
CPC ..... C07J 63/008; C07J 73/003; C07D 311/78; C07D 493/04; A61K 31/585; A61K 31/366; A61P 35/00
See application file for complete search history.

(56) References Cited

PUBLICATIONS

Lobastova et al., Microbiological Synthesis of Stereoisomeric 7(alpha/beta)-hydroxytestololactones and 7(alpha/beta)-hydroxytestolactones, Applied Microbiology and Biotechnology, vol. 103, No. 12, pp. 4967-4976 (Year: 2019).*

* cited by examiner

*Primary Examiner* — Brenda L Coleman

(57) ABSTRACT

Biotransformation of an aromatase inhibitor, testolactone (1), yielded four metabolites, 7β-hydroxy-3-oxo-13,17-seco-5β-androsta-1-eno-17,13α-lactone (2), 3α,11β-dihydroxy-13,17-seco-5β-androsta-17,13α-lactone (3), 4β,5β-epoxy-3β-hydroxy-13,17-secoandrosta-1-eno-17,13α-lactone (4), and 4β,5β-epoxy-3α-hydroxy-13,17-secoandrosta-1-eno-17,13α-lactone (5). Aromatase (estrogen synthase) involves in the synthesis of estrogen, and promotes the growth of breast cancerous cells. It is a key target for the discovery of chemotherapeutic agents against ER+(estrogen-positive) breast-cancers. Metabolites 2 ($IC_{50}$=8.63±0.402 nM), and 3 ($IC_{50}$=9.23±1.31 nM) were identified as potent inhibitors against human aromatase enzyme, in comparison to 1 ($IC_{50}$=0.716±0.031 μM), and the standard aromatase inhibiting drug, exemestane ($IC_{50}$=0.232±0.031 μM). Derivatives 4 ($IC_{50}$=10.37±0.50 μM) and 5 ($IC_{50}$=0.82±0.059 μM) also showed a good inhibition against aromatase enzyme. Therefore, metabolites 2-5 have the potential to serve as therapeutic agents against ER+ (estrogen-positive) breast-cancers.

2 Claims, 2 Drawing Sheets

POTENT AROMATASE INHIBITORS THROUGH FUNGAL TRANSFORMATION OF ANTI-CANCER DRUG TESTOLACTONE: AN APPROACH TOWARDS TREATMENT OF BREAST CANCER

BACKGROUND OF THE INVENTION

Breast cancers are highly prevalent life-threatening cancers, affecting millions of women every year globally. They are diverse and heterogeneous groups of diseases at histological, molecular, and systemic levels, having various implications for physicians, and patients. Around 80% of breast cancers are estrogen dependent (ER+), require estrogens for their growth. Estrogens are hormones that play an important role in the reproduction, and in the development of female organs. The increased level of estrogens due to the overexpression of estrogen synthase (aromatase) in the body, promotes the growth of breast tumors. Aromatase is an enzyme that catalyzes the conversion of androgen to estrogen, i.e., steroidal ring "A" into aromatic state. Therefore, inhibition of aromatase enzyme can effectively lower the production of estrogens. Estrogen responsive breast cancer can thus be treated by inhibiting the action of aromatase enzyme in the body.

Currently available aromatase inhibitors have many adverse effects on human body, including nausea, headache, osteoporosis, fatigue, hot flushes, skin reactions, and cardiovascular diseases. This makes them difficult to tolerate for 2-5 years, required for the effective post-surgical treatment of ER+ breast cancer. It would, therefore, be a great advantage to develop even more potent aromatase inhibitors with better pharmacodynamic profiles.

Testolactone (1) (3-oxo-13,17-secoandrosta-1,4-dieno-17,13α-lactone), a synthetic steroidal anti-cancer drug, was previously marketed under the brand name of Teslac for the treatment of estrogen responsive breast cancer. The preliminary action of testolactone (1) is the inhibition of aromatase enzyme to block the production of estrogens, and to prevents the growth of cancer cells in breasts. Compound 1 has also been reported as anti-estrogens and anti-carcinogens, and for the treatment of disorders due to the imbalance between androgen and estrogen actions, such as gynecomastia, and prostate cancer and prostatic hyperplasia Whole-cell biocatalysis is a robust approach to synthesize compounds whose structures resemble to parent drugs (substrate). This technique is effectively used where synthetic methodologies are expensive, and difficult. It is a selective, low-cost, and eco-friendly technique, involves the use of bacteria, fungi, yeast, plants, etc. Participation of a variety of enzymes during the biotransformation by whole-cell systems yields regio-, chemo-, and stereo-selective analogues of existing drugs, eliminating the use of toxic and expensive catalysts and reagents.

BRIEF SUMMARY OF THE INVENTION

In continuation of our fungal-mediated bio-transformational research on biologically active steroids and on the basis of reported biological importance of testolactone (1), we focused on whole-cell biocatalysis of compound 1 by using fungi. In the present research work, biotransformation of testolactone (1) with *Macrophomina phaseolina* was carried out at room temperature using aqueous media. This yielded four metabolites, 7β-hydroxy-3-oxo-13,17-seco-5β-androsta-1-eno-17,13α-lactone (2), 3α,11β-dihydroxy-13,17-seco-5β-androsta-17,13α-lactone (3), 4β,5β-epoxy-3β-hydroxy-13,17-secoandrosta-1-eno-17,13α-lactone (4), and 4β,5β-epoxy-3α-hydroxy-13,17-secoandrosta-1-eno-17,13α-lactone (5). Their structures were determined by $^1$H-, $^{13}$C-, and 2D-NMR, HREI-MS, HRFAB-MS, and IR spectral data.

In general, aromatase enzyme is present in high quantity in placenta, and in granulosa cells of ovarian follicles, depending on stimulation of cyclical gonadotropin. In the current study, the anti-aromatase activity of structural analogues 2-5, of anti-cancer aromatase inhibitor testolactone (1) was determined in a pool of human fresh placental microsomes in vitro.

Based on reported anti-aromatase activity of drug 1, transformed products 2-5 were evaluated against human placental microsomal aromatase to check their level of differential inhibition potential against the enzyme. Among them, metabolites 2 ($IC_{50}$=0.00863±0.0004 μM; 8.63±0.402 nM), and 3 ($IC_{50}$=0.00923±0.0013 μM; 9.23±1.310 nM) were identified as potent inhibitors against aromatase, in comparison to the substrate (anti-cancer aromatase inhibitor testolactone, 1) ($IC_{50}$=0.716±0.031 μM), and the standard aromatase inhibitor, exemestane ($IC_{50}$=0.232±0.031 μM). Derivatives 4 ($IC_{50}$=10.37±0.50 μM), and 5 ($IC_{50}$=0.82±0.059 μM) also showed a good inhibitory potential against aromatase enzyme.

Metabolites 2-5 were identified as non-cytotoxic against breast cancer cell lines, e.g., MCF-7, MDA-MB-231, and BT-474. Transformed products 2-5 were found to be inactive to normal cell lines, including BJ (human fibroblast), and 3T3 (mouse fibroblast).

DETAILED DESCRIPTION OF THE INVENTION

Experimental

Media Preparation

Figure 1:
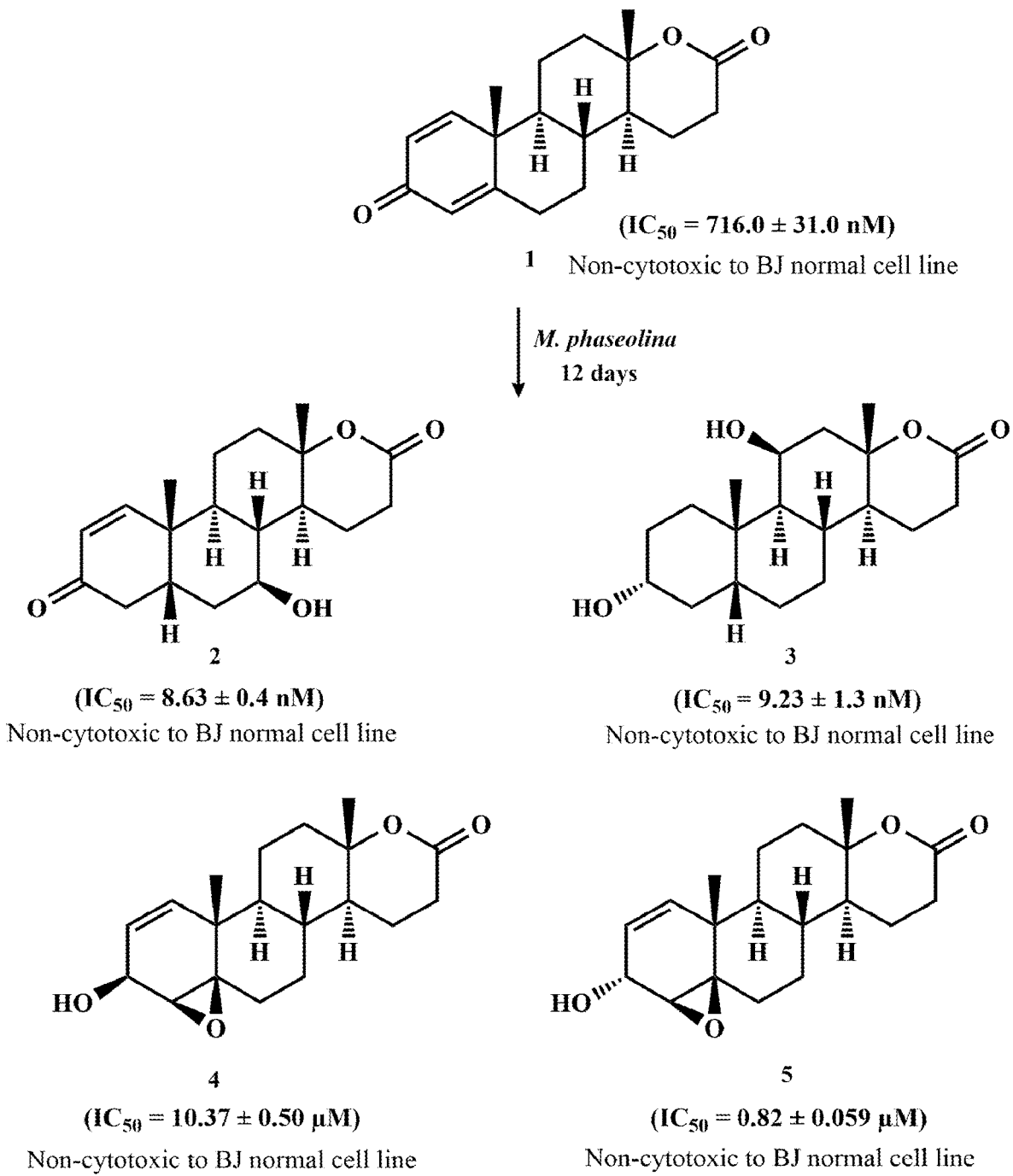
FIG. 1 depicts the structures of testolactone (1) and its metabolites, 7β-hydroxy-3-oxo-13,17-seco-5β-androsta-1-eno-17,13α-lactone (2) 3α,11β-dihydroxy-13,17-seco-5β-androsta-17,13α-lactone (3), 4β,5β-epoxy-3β-hydroxy-13,17-secoandrosta-1-eno-17,13α-lactone (4), and 4β,5β-epoxy-3α-hydroxy-13,17-secoandrosta-1-eno-17,13α-lactone (5) via *M. phaseolina*-mediated transformation of drug 1, along with their aromatase inhibition and cytotoxic activities against human fibroblast (BJ) and mouse fibroblast (3T3) cell lines.
Figure 2:
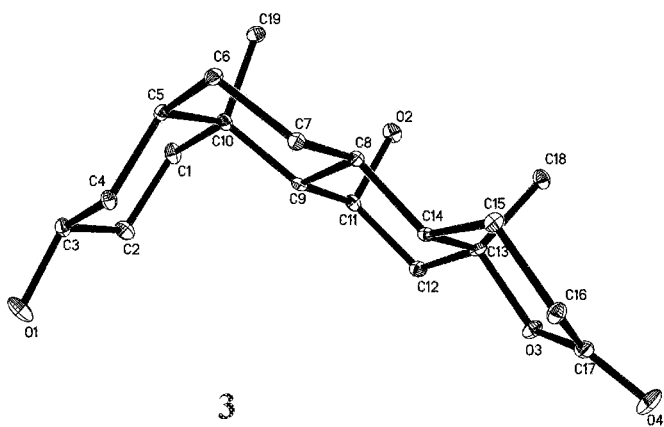
FIG. 2 depicts the computer-generated ORTEP drawing of final X-ray models of derivatives 3-5.
Figure 2:
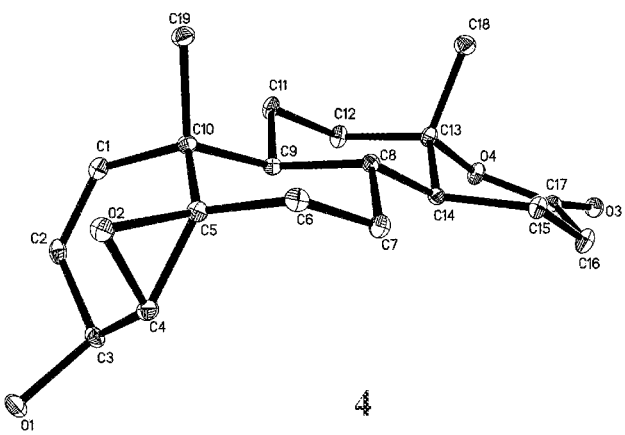
Figure 2:
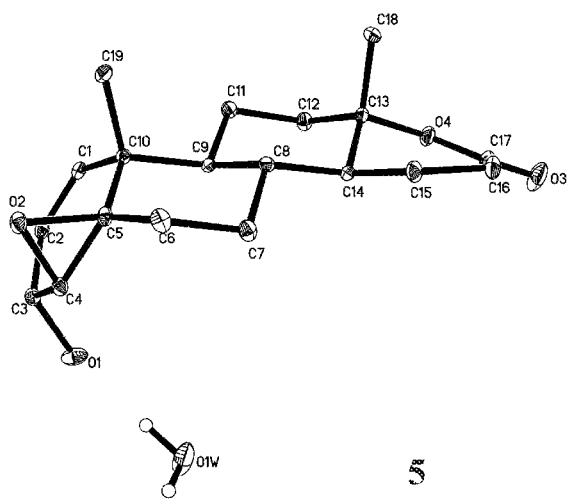

One-liter media for the maximum growth of fungus (*Macrophomina phaseolina*, KUCC 730 (Karachi University Culture Collection, Pakistan), was prepared by mixing 10 g glucose, 5 g NaCl, 5 g peptone, 5 g $KH_2PO_4$, and 10 mL glycerol in 1 L distilled water, and autoclaved for their maximum, and mature growth.

Fermentation

On the basis of small-scale screening results, 4 L of media for fungus was prepared by mixing aforementioned ingredients. Media (4 L) was distributed into 20 Erlenmeyer flasks of 500 mL (200 mL in each), cotton plugged, and autoclaved at 121° C. The sterilized media was then cooled at room temperature, and inoculated with seed flasks of *Macrophomina phaseolina* cell culture under sterilized conditions. Fungal cell cultures containing flasks were placed for 3-4 days on rotary shaker (121 rpm). After the mature growth of *M. phaseolina* in each flask, 1 g of testolactone (1) ($C_{19}H_{24}O_3$) ((Cas No. 968-93-4) was procured from Fartop Limited, China) was dissolved in 10 mL of DMSO and dispensed (2 mL) in each fungal culture containing flasks. The flasks were then again placed on rotary shaker (121 rpm) at 25° C. for twelve days.

Extraction

After incubation, the reaction was stopped by addition of DCM (dichloromethane) in each flask, and filtered to separate fungal masses. Each filtrate (aqueous and organic phases) was separated by extracting with 20 L of DCM. Anhydrous $Na_2SO_4$ (sodium sulfate) was added in each organic layer to make them moisture free, filtered, and concentrated under reduced pressure.

Isolation and Purification

The resulting crude (2 g) was fractionated by column chromatography (CC) with a mobile phase of hexanes-acetone. The polarity of mobile phase was increased by increasing 5-100% gradients of acetone. As a result, four main fractions, i.e., 1-4 were obtained, which were analyzed by thin layer chromatography (TLCs). The fractions were further purified through recycling reverse phase HPLC (LC-908; equipped with YMC M-80; 20-250 mm i.d. 4-5 μm). Compounds 2 (methanol-water; 7/3, $R_T$=32 min, 22.3 mg), 3 (methanol-water; 6/4, $R_T$=36 min, 24.2 mg), 4 (methanol-water; 7/3, $R_T$=36 min, 8.1 mg), and 5 (methanol-water; 7/3, R T=31 min, 7.1 mg) were purified from fractions 1-4, respectively. Substrate 1 was also recovered.

7β-Hydroxy-3-oxo-13,17-seco-5β-androsta-1-eno-17,13α-lactone (2)

White solid; m. p. 197-199° C.; $[\alpha]_D^{25}$=+231.3 (c 0.001, MeOH); IR ($CH_3Cl$): $\nu_{max}$ ($cm^{-1}$) 3455 (OH), 2942 (CH), 1675 (α,β-unsaturated ketone), 1714 (6-membered lactone carbonyl); HREI-MS m/z 318.1844 [$M^+$] ($C_{19}H_{26}O_4$) (calcd. 318.1831); EI-MS m/z: 318.3 [$M^+$]; $^1$H-NMR (δ) ($CDCl_3$), H-1 (6.81, d, $J_{1,2}$=10.2 Hz), H-2 (5.96, d, $J_{2,1}$=10.2 Hz), $H_2$-4 (2.60, overlap; 2.35, dd, $J_{4a,4b}$=17.2 Hz; $J_{4,5}$=4.4 Hz), H-5 (2.20, m), $H_2$-6 (1.86, overlap; 1.76, overlap), H-7 (3.79, m), H-8 (δ 1.35, overlap), H-9 (1.62, m), $H_2$-11 (1.74, overlap; 1.51, m), $H_2$-12 (2.08, dt, $J_{12,12}$=12.6 Hz; $J_{12,11}$=3.1 Hz), H-14 (δ 1.69, overlap), $H_2$-15 (δ 2.61, overlap; 1.85, overlap), $H_2$-16 (δ 2.68, overlap; 2.52, overlap), $H_3$-18 (1.36, s), $H_3$-19 (1.21, s); $^{13}$C-NMR (δ) ($CDCl_3$), C-1 (159.2), C-2 (127.9), C-3 (198.6), C-4 (39.4), C-5 (40.7), C-6 (37.4), C-7 (70.1), C-8 (44.6), C-9 (46.8), C-10 (37.9), C-11 (23.5), C-12 (39.4), C-13 (83.2), C-14 (44.0), C-15 (21.9), C-16 (29.0), C-17 (171.2), C-18 (20.4), C-19 (20.7).

3α,11β-Dihydroxy-13,17-seco-5β-androstano-17,13α-lactone (3)

White solid; m. p. 188-191° C.; $[\alpha]_D^{25}$=+11.6 (c 0.001, MeOH); IR ($CH_3Cl$): $\nu_{max}$ ($cm^{-1}$) 3431 (OH), 2931 (CH), 1702 (6-membered lactone carbonyl); HRFAB-MS (+ve) m/z 323.2233 [$M+H$]$^+$ ($C_{19}H_{34}O_4$) (calcd. 323.2222); FAB-MS (+ve) m/z 323.1 [$M+H$]$^+$; FAB-MS (-ve) m/z 321.2 [$M-H$]$^-$; $^1$H-NMR (δ) ($CDCl_3$), $H_2$-1 (1.89, overlap; 1.22, overlap), $H_2$-2 (1.71, overlap; 1.29, overlap), H-3 (3.64, m), $H_2$-4 (1.68, overlap; 1.53, overlap), H-5 (1.66, overlap), $H_2$-6 (1.73, overlap; 1.28, overlap), $H_2$-7 (1.83, overlap; 1.12, overlap), H-8 (1.69, overlap), H-9 (1.51, overlap), H-11 (4.32, br. d, $J_{e,a}$=1.7 Hz), $H_2$-12 (2.08, dd, $J_{12,12}$=13.8 Hz; $J_{12,11e}$=3.1 Hz; 1.81, overlap), H-14 (1.30, overlap), $H_2$-15 (1.99, overlap; 1.50, overlap), $H_2$-16 (2.66, ddd, $J_{16,16}$=19.1 Hz; $J_{16a,15a}$=8.9; $J_{16a,15b}$=2.1 Hz; 2.53, m), $H_3$-18 (1.46, s), $H_3$-19 (1.09, s); $^{13}$C-NMR (δ) ($CDCl_3$), C-1 (35.0), C-2 (30.7), C-3 (71.4), C-4 (36.0), C-5 (42.4), C-6 (25.8), C-7 (26.0), C-8 (33.1), C-9 (48.0), C-10 (34.8), C-11 (66.6), C-12 (47.4), C-13 (82.6), C-14 (43.7), C-15 (19.6), C-16 (28.7), C-17 (171.5), C-18 (23.2), C-19 (26.4); Single-crystal X-ray Data: crystal system, orthorhombic; space group, $P2_12_12_1$; unit cell dimensions, a=6.4517 (2) Å, α=90, b=12.2365 (3) Å, β=90, c=21.1261 (5) Å, γ=90; volume, 1667.83 (8) Å$^3$; crystal size, 0.11×0.10×0.05 mm; density, 1.284 mg/m$^3$; θ range, 4.18 to 68.22.

4β,5β-Epoxy-3β-hydroxy-13,17-secoandrosta-1-eno-17,13α-lactone (4)

White solid; m. p. 192-193° C.; $[\alpha]_D^{25}$=+302.0 (c 0.001, MeOH); IR ($CH_3Cl$): $\nu_{max}$ ($cm^{-1}$) 3434 (OH), 2944 (CH), 1720 (6-membered lactone carbonyl); HR-EIMS m/z 318.1832 [$M^+$] ($C_{19}H_{26}O_4$) (calcd. 318.1831); EI-MS m/z: 318.1 [$M^+$]; $^1$H-NMR (δ) ($CDCl_3$), H-1 (5.43, overlap), H-2 (5.41, overlap), H-3 (4.44, br. d, $J_{3,2}$=$J_{3,4}$=2.5 Hz), H-4 (3.29, br. d, $J_{4,3}$=1.5 Hz), $H_2$-6 (2.12, td, $J_{6a,6b}$=13.7; $J_{6,7}$=4.4 Hz; 1.21, m), $H_2$-7 (1.99, overlap; 1.08, overlap), H-8 (1.26, m), H-9 (1.04, m), $H_2$-11 (1.73, m; 1.37, overlap), $H_2$-12 (1.92, m; 1.59, m), H-14 (1.38, m), $H_2$-15 (1.99, m; 1.51, m), $H_2$-16 (2.67, m; 2.57, m), $H_3$-18 (1.31, s), $H_3$-19 (1.09, s); $^{13}$C-NMR (δ) ($CDCl_3$), C-1 (134.9), C-2 (124.2), C-3 (65.5), C-4 (63.5), C-5 (65.2), C-6 (30.4), C-7 (28.9), C-8 (37.5), C-9 (51.7), C-10 (39.2), C-11 (23.0), C-12 (39.0), C-13 (82.8), C-14 (45.6), C-15 (19.9), C-16 (28.5), C-17 (171.1); C-18 (20.0); C-19 (16.3); Single-crystal X-ray Data: crystal system, orthorhombic; space group, $P2_12_12_1$; unit cell dimensions, a=7.0877 (2) Å, α=90, b=11.0304 (3) Å, β=90, c=20.3492 (5) Å, γ=90; volume, 1590.90 (7) Å$^3$; crystal size, 0.24×0.15×0.11 mm; density, 1.329 mg/m$^3$; θ range, 4.35 to 68.15.

4β,5β-Epoxy-3α-hydroxy-13,17-secoandrosta-1-eno-17,13α-lactone (5)

White solid; m. p. 194-196° C.; $[\alpha]_D^{25}$=+28.6 (c 0.001, MeOH); IR ($CH_3Cl$): $\nu_{max}$ ($cm^{-1}$) 3437 (OH), 2944 (CH), 1720 (6-membered lactone carbonyl); HREI-MS m/z 318.1838 [$M^+$] ($C_{19}H_{26}O_4$) (calcd. 318.1831); EI-MS m/z (%): 318.1 [$M^+$] (54), 300.2 (49), 227.1 (23), 199.1 (21), 147.1 (37), 121.1 (100); $^1$H-NMR (δ) ($CDCl_3$), H-1 (5.59, overlap), H-2 (5.57, overlap), H-3 (4.50, br. t, $J_{3,2}$=$J_{3,4}$=1.4 Hz), H-4 (3.08, br. d, $J_{4,3}$=1.6 Hz), $H_2$-6 (2.15, overlap; 1.29, overlap), $H_2$-7 (2.01, overlap; 1.18, overlap), H-8 (1.31, overlap), H-9 (1.33, overlap), $H_2$-11 (1.71, overlap; 1.37, overlap), $H_2$-12 (1.98, overlap; 1.65, overlap), H-14 (1.46, m), $H_2$-15 (2.02, overlap; 1.55, overlap), $H_2$-16 (2.72, ddd, $J_{16,16}$=18.8 Hz; $J_{16a,15a}$=8.1 Hz; $J_{16a,15b}$=2.0 Hz; 2.65, m), $H_3$-18 (1.33, s), $H_3$-19 (1.11, s); $^{13}$C-NMR (δ) ($CDCl_3$), C-1 (137.2), C-2 (122.5), C-3 (64.2), C-4 (62.0), C-5 (63.7), C-6 (30.2), C-7 (28.7), C-8 (38.0), C-9 (52.9), C-10 (39.4), C-11 (22.7), C-12 (38.9), C-13 (82.9), C-14 (45.5), C-15 (19.9), C-16 (28.6), C-17 (171.1), C-18 (20.0), C-19 (16.9). Single-crystal X-ray Data: crystal system, monoclinic; space group, $P2_1$; unit cell dimensions, a=5.9716 (15) Å, α=90, b=14.040 (4) Å, =100.909 (17), c=10.445 (2) Å, γ=90; volume, 860.0 (4) Å$^3$; crystal size, 0.180×0.170×0.080 mm; density, 1.299 mg/m$^3$; θ range, 4.310 to 68.221.

Human Placental Aromatase Inhibition Assay Protocol

The aromatase enzyme activity can be determined by measuring conversion of testosterone to 17β-estradiol, shown as follows:

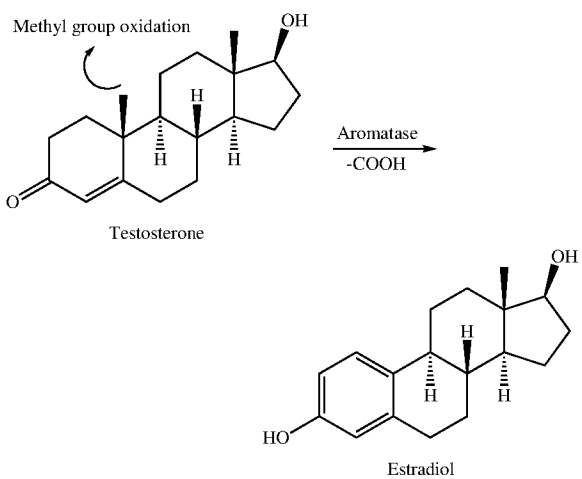

The activity is determined in a 1 mL reaction mixture, containing protein (mainly aromatase enzyme) (2 mg/mL), testosterone (10 µM), potassium phosphate buffer (0.1 M) at pH 7.4, and 101.11, of test compound (0.1 mM). The reaction mixture was pre-incubated at 37° C. for 10 min. NADPH (1 mM) was then added, and incubated for 20 min. The reaction was terminated by adding 100 µL of trichloroacetic acid (10%, w/v). The reaction mixture was centrifuged for 10 min at 12,000 g, pellet was discarded, and the supernatant containing 17β-estradiol was extracted with 1 mL N-butylchloride. The extracted 17β-estradiol was then dried and the quantity of the product was determined by UPLC (column ACE Generix 5 µm $C_{18}$ 150×4.6 mm) using isocratic elution of the mobile phase containing triethylamine (0.1%) in $ACN/H_2O$ (45:55, v/v), and pH 3.0 (adjusted by orthophosphoric acid) with a flow rate of 1.2 mL/min at 200 nm. Calculations were performed by following formula:

$$\% \text{ Inhibition} = 100 - \frac{\text{(Peak area of test sample)}}{\text{(Peak area of control)}} \times 100$$

Results and Discussion

The HREI-MS of metabolite 2 displayed the [M+] at m/z 318.1844 ($C_{19}H_{26}O_4$), indicating addition of an oxygen atom, along with two hydrogen atoms in substrate 1 (m/z 300). Reduction between C-4/C-5 was inferred via $^3J$ correlation of $H_2$-6 and H-1 with C-4. Hydroxyl group at C-7 was supported by HMBC correlations of H-7 with C-5, C-8 and C-9, and $H_2$-6 with C-7. The structure of compound 2 was identified as 7β-hydroxy-3-oxo-13,17-seco-5β-androsta-1-eno-17,13α-lactone.

The [M+H]+ of metabolite 3 was observed at m/z 323.2233 in the HRFAB-MS (high resolution fast atom bombardment spectrometry), 22 amu greater than the substrate 1 (m/z 300). Reduction in the ring A of derivative 3 was inferred through the HMBC correlations of $H_2$-1 and $H_2$-4 with C-2, C-3 and C-10. An OH group was placed at C-11, based on HMBC correlations of H-11 with C-9, C-10, and C-12. The structure of derivative 3 was determined as 3α,11β-dihydroxy-13,17-seco-5β-androstano-17,13α-lactone.

The HREI-MS of metabolite 4 presented its [M+] at m/z 318.1832, indicating addition of oxygen, and two hydrogen atoms in substrate 1 (m/z 300). Epoxidation between C-4/C-5, along with reduction at C-3 was inferred though the $^2J$ and $^3J$ correlations of H-2 with C-3 and C-4. The structure was deduced as 4β,5β-epoxy-3β-hydroxy-13,17-secoandrosta-1-eno-17,13α-lactone (4).

The [M+] of metabolite 5 in the HREI-MS was observed at m/z 318.1838, indicating the addition of an oxygen atom, along with two hydrogen atoms in substrate 1 (m/z 300). Reduction at C-3, along with epoxidation between C-4/C-5 was determined via the HMBC correlations of H-1 with C-5, and H-2 with C-3 and C-4. The structure of derivative 5 was identified as 4β,5β-epoxy-3α-hydroxy-13,17-secoandrosta-1-eno-17,13α-lactone.

Placement of β-OH at C-7, along with reduction between C-4/C-5 in compound 2 ($IC_{50}$=0.00863±0.0004 µM) has increased its anti-aromatase activity than substrate 1 ($IC_{50}$=0.716±0.031 µM). Similarly, β-OH at C-11, and reduction of olefinic groups at C-1, C-2, C-4, and C-5, and ketonic carbonyl C-3 into secondary alcohol (α-OH) in compound 3 ($IC_{50}$=0.00923±0.0013 µM) also increased its anti-aromatase activity. While epoxidation between C-4/C-5, along with reduction of ketone into alcohol (α-OH) in compound 5 ($IC_{50}$=0.82±0.059 µM) has not much affected its inhibition potential against placental microsomal aromatase. Likewise, epoxidation between C-4/C-5, along with reduction of ketone into alcohol (β-OH) in derivative 4 ($IC_{50}$=10.37±0.50 µM) has decreased its anti-aromatase activity, as compared to parent molecule, testolactone (1), and derivatives 2, 3, and 5.

Presence of hormone receptors, such as estrogen receptor (ER), progesterone receptor (PR), and human epidermal growth factor receptor (HER2) in breast cancer cell lines make them responsive towards hormonal therapies. While the breast cancer negative for these hormone receptors are more difficult to treat, as they do not respond to hormonal therapies. High amount of estrogens in the body due to overexpression of aromatase enzyme, enhances the breast tumors growth. In general, breast cancer tissues have been reported to express more aromatase enzyme than the normal tissues of breast. Estrogens and androgens stimulate the growth of MCF-7 breast cancer cells. Derivatives 2-5 were found to be inactive to breast cancer cell lines, e.g., MCF-7 (ER+, PR+, and $HER_2$+), MDA-MB-231 (ER−, PR−, and $HER_2$−), and BT-474 (ER+, and $HER_2$+) in vitro. This showed structural alteration, in anti-cancer drug, testolactone (1) did not affect their cytotoxicity potential.

What is claimed is:

1. A testolactone derivative selected from the group consisting of 7β-hydroxy-3-oxo-13,17-seco-5β-androsta-1-eno-17,13α-lactone (2), 3α,11β-dihydroxy-13,17-seco-5β-androsta-17,13α-lactone (3), 4β,5β-epoxy-3β-hydroxy-13,17-secoandrosta-1-eno-17,13α-lactone (4), and 4β,5β-epoxy-3α-hydroxy-13,17-secoandrosta-1-eno-17,13α-lactone (5) and a pharmaceutically acceptable salt thereof.

2. A method of treating estrogen-responsive (ER+) breast cancer, the method comprising on administration of effective amount of testolactone derivative selected from the group consisting of 7β-hydroxy-3-oxo-13,17-seco-5β-androsta-1-eno-17,13α-lactone (2), 3α,11β-dihydroxy-13,17-seco-5β-androsta-17,13α-lactone (3), 4β,5β-epoxy-3β-hydroxy-13,17-secoandrosta-1-eno-17,13α-lactone (4), and 4β,5β-epoxy-3α-hydroxy-13,17-secoandrosta-1-eno-17,13α-lactone (5) or their salts in suitable pharmaceutical excipients, adjuvant, carrier, or diluent to subject in need thereof.

* * * * *